United States Patent
Su et al.

(10) Patent No.: US 11,026,607 B2
(45) Date of Patent: Jun. 8, 2021

(54) REGIONAL SATURATION SHOCK DETECTION METHOD AND SYSTEM

(71) Applicant: Covidien LP, Mansfield, MA (US)

(72) Inventors: Mark Yu-Tsu Su, Boulder, CO (US); Ulf Rune Borg, Longmont, CO (US)

(73) Assignee: Covidien LP, Mansfield, MA (US)

( * ) Notice: Subject to any disclaimer, the term of this patent is extended or adjusted under 35 U.S.C. 154(b) by 334 days.

(21) Appl. No.: 16/123,803

(22) Filed: Sep. 6, 2018

(65) Prior Publication Data

US 2019/0000363 A1   Jan. 3, 2019

Related U.S. Application Data

(63) Continuation of application No. 14/640,928, filed on Mar. 6, 2015, now Pat. No. 10,098,576.

(60) Provisional application No. 61/979,304, filed on Apr. 14, 2014, provisional application No. 61/953,442, filed on Mar. 14, 2014.

(51) Int. Cl.
| | | |
|---|---|---|
| *A61B 5/0205* | (2006.01) | |
| *A61B 5/1455* | (2006.01) | |
| *A61B 5/021* | (2006.01) | |
| *A61B 5/026* | (2006.01) | |

(52) U.S. Cl.
CPC ........ *A61B 5/14552* (2013.01); *A61B 5/0205* (2013.01); *A61B 5/14551* (2013.01); *A61B 5/0261* (2013.01); *A61B 5/02125* (2013.01)

(58) Field of Classification Search
CPC . A61B 5/0205; A61B 5/1455; A61B 5/14551; A61B 5/14552; A61B 5/0261; A61B 5/02125; A61B 5/1459; A61B 5/4833; A61B 5/4836; A61B 5/4839; A61B 5/4848
See application file for complete search history.

(56) References Cited

U.S. PATENT DOCUMENTS

| | | |
|---|---|---|
| 5,139,025 A | 8/1992 | Lewis et al. |
| 5,217,013 A | 6/1993 | Lewis et al. |
| 6,400,972 B1 | 6/2002 | Fine |
| 7,319,894 B2 | 1/2008 | Higgins |
| 7,426,407 B2 | 9/2008 | Higgins |
| 7,532,919 B2 | 5/2009 | Soyemi |
| 8,483,789 B2 | 7/2013 | Higgins |
| 8,588,878 B2 | 11/2013 | Li et al. |
| 9,095,291 B2 | 8/2015 | Soller et al. |
| 9,622,694 B2 | 4/2017 | Mao et al. |
| 10,098,576 B2 | 10/2018 | Su et al. |
| 2009/0326386 A1 | 12/2009 | Sethi et al. |

(Continued)

OTHER PUBLICATIONS

Management of Shock, Part 7 of Pediatric Advanced Life Support Provider Manual, American Heart Association, Oct. 2011, pp. 85-108.

(Continued)

*Primary Examiner* — Chu Chuan Liu
(74) *Attorney, Agent, or Firm* — Shumaker & Sieffert, P.A.

(57) ABSTRACT

According to various embodiments, a medical system and method for early detection of shock may include devices configured to provide information about multiple patient parameters. In certain embodiments, the system may receive input from a regional saturation sensor. Based on these inputs, the system may provide a diagnosis of shock and/or distinguish between various types of shock.

27 Claims, 6 Drawing Sheets

(56) References Cited

U.S. PATENT DOCUMENTS

2010/0292549 A1\* 11/2010 Shuler .................. A61B 5/1455
600/324
2011/0201905 A1    8/2011  Spencer
2013/0030267 A1    1/2013  Lisogurski et al.
2013/0096401 A1    4/2013  Lash et al.

OTHER PUBLICATIONS

Lichtenstern et al., "Near-infrared Spectroscopy in Sepsis Therapy: Predictor of a Low Central Venous Oxygen Saturation," Anaesthesist, Sep. 27, 2012, pp. 883-890 (Translation is provided for only the Abstract).

Ranucci et al., "Near-infrared Spectroscopy Correlates with Continuous Superior Vena Cava Oxygen Saturation in Pediatric Cardiac Surgery Patients," Pediatric Anesthesia, vol. 18, Sep. 3, 2008, pp. 1163-1169.

Schereen et al., "Monitoring Tissue Oxygenation by Near Infrared Spectroscopy (NIRS): Background and Current Applications," Journal of Clinical Monitoring and Computing, vol. 26, Mar. 31, 2012, pp. 279-287.

Recognition of Shock, Part 6 of Pediatric Advanced Life Support Provider Manual, American Heart Association, Oct. 2011, pp. 69-83.

Prosecution History from U.S. Appl. No. 14/640,928, dated Aug. 4, 2017 through Aug. 29, 2018, 57 pp.

\* cited by examiner ustom # REGIONAL SATURATION SHOCK DETECTION METHOD AND SYSTEM

CROSS-REFERENCE TO RELATED APPLICATIONS

This application is a continuation of U.S. patent application Ser. No. 14/640,928, filed Mar. 6, 2015, which claims the benefit of U.S. Provisional Patent Application No. 61/953,442, filed Mar. 14, 2014, and U.S. Provisional Patent Application No. 61/979,304, filed on Apr. 14, 2014, each of which are hereby incorporated by reference in their entirety.

BACKGROUND

The present disclosure relates generally to a method and system for monitoring physiological parameters of a patient. Specifically, embodiments of the disclosure relate to the assessment of shock using regional saturation data.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare, monitor the progress of patient care, and detect changing conditions that potentially need attention. As a result, such monitoring devices have become an indispensable part of modern medicine.

Further, for complex clinical conditions, information representative of multiple physiological parameters may be used to diagnose or detect conditions that have widespread physiological effects. For example, shock is a clinical syndrome that, in certain cases, may be characterized by decreased blood flow to the capillary beds. This condition typically occurs when arterial pressure and subsequently tissue blood flow decrease to a degree that the amount of delivered oxygen is inadequate to meet the metabolic needs of the tissue. During shock, the body directs blood to the heart and the brain, often at the expense of relatively less important organs such as the liver, skin, muscle, and gut. However, monitoring such changes in blood flow towards primary organs and away from secondary organs may be challenging, particular for patients who are ill or for pediatric patients.

BRIEF DESCRIPTION

Provided herein are non-invasive monitoring techniques that are capable assessing shock. The disclosed embodiments include a monitor including light drive circuitry configured to drive a light emitter coupled to a regional saturation sensor; input circuitry configured to receive a regional saturation signal from a first detector and a second detector of the regional saturation sensor, wherein the first detector and the second detector are spaced apart from the light emitter at respective first and second distances, the second distance being greater than the first distance; a processor configured to execute instructions to: determine a regional saturation parameter based on the regional saturation signal, wherein determining the regional saturation parameter comprises assessing a portion of the signal that is representative of light detected by the second detector that has passed through additional tissue relative to the first detector; receive information related to a blood pressure parameter of the patient; determine that the patient is in shock when a relationship between the regional saturation parameter and the blood pressure parameter is indicative of shock; and provide an output related to shock when a determination of shock has been made; and a memory storing the instructions.

Also provided herein is a method including the steps of receiving a regional saturation signal over a period of time from a first detector and a second detector of a regional saturation sensor, wherein the first detector and the second detector are spaced apart from an emitter at respective first and second distances, the second distance being greater than the first distance; determining a baseline regional saturation based on the regional saturation signal during a first window in the period of time; determining a regional saturation parameter based on the regional saturation signal during a second window in the period of time, wherein the second window is after the first window, wherein determining the baseline regional saturation and the regional saturation parameter comprises assessing a portion of the signal that is representative of light detected by the second detector that has passed through additional tissue relative to the first detector; providing an indication of possible shock when the regional saturation is below the baseline; monitoring the regional saturation during and after administration of a treatment for shock; determining if the patient is fluid-responsive based on whether the regional saturation parameter increases during or after the treatment for shock; and providing an indication of fluid-responsiveness when the regional saturation parameter increases during or after the treatment for shock.

Also provided herein is a system that includes one or more light emitters; a plurality of detectors that, in operation, detect the light to generate a first signal representative of a regional saturation of the patient; and a non-invasive blood pressure sensor that, in operation, generates a second signal representative of a blood pressure of the patient; and a monitor configured to: receive the first signal and determine a regional saturation of the patient based on the first signal; receive the second signal and determine a blood pressure of the patient based on the second signal; and determine that the patient is in shock when a relationship between the regional saturation and the blood pressure is indicative of shock; and determine that the patient is not in shock when the relationship between the regional saturation and the blood pressure is not indicative of shock.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
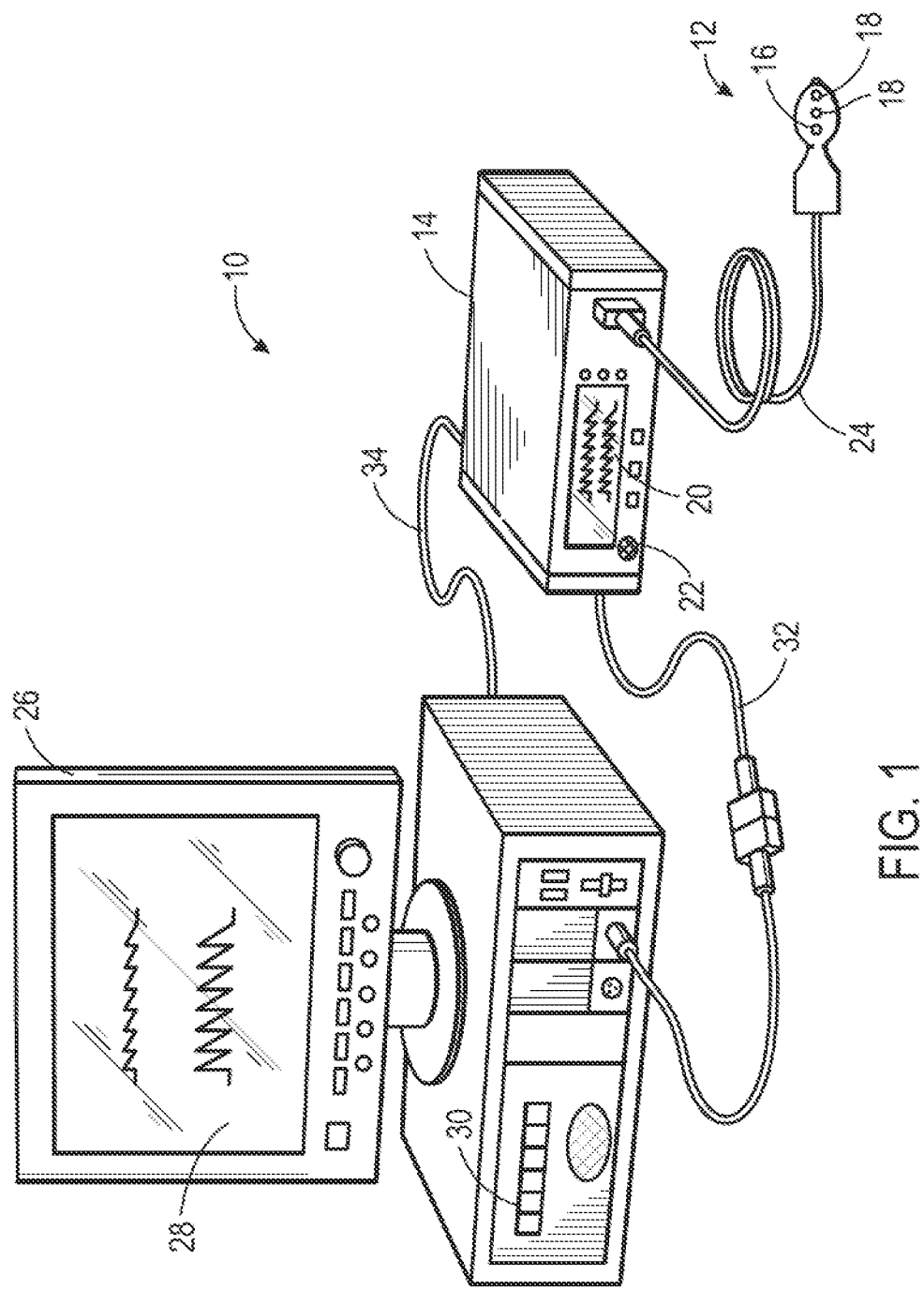
FIG. 1 is a front view of an embodiment of a monitoring system configured to be used to detect shock in a patient.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Physiological shock may result from any serious assault on the body's homeostatic mechanisms, whether from hemorrhage, trauma, burn injury, myocardial infarction or sepsis. Shock may involve widespread hypoperfusion at the tissue level, due to reduction of blood volume, reduction of cardiac output or redistribution of effective circulation. Early detection of shock permits caregivers to proceed with appropriate therapy (e.g., pharmaceutical intervention, fluid). In one technique, an invasive measurement of central or mixed venous saturation is used to assess altered perfusion, which may be associated with shock. However, invasive measurements to detect blood parameters may not be desirable in certain patients. Further, invasive central or mixed venous measurements provide a global measure of venous perfusion rather than a local measure. Global measurements may not accurately reflect local differences in end-organ perfusion, i.e., in the brain, that may be indicative of shock. Other techniques combine information related to blood parameters with clinical observations, such as altered mental status. However, such clinical observations may depend on the skill level of the caregiver and provide periodic, and not continuous, information about a patient's clinical condition.

Provided herein are techniques for detection of shock that include monitoring regional saturation in a patient by non-invasively estimating the oxygenation of an interrogated region of a patient. Such regional saturation techniques may replace or, alternatively, be used in addition to central or mixed venous saturation measurements. Regional saturation provides a local measurement that may be used, for example, in conjunction with additional patient information for patient monitoring, early diagnosis and detection of shock, therapeutic guidance during intervention or resuscitation, assessment of the results of any intervention, or post-intervention or resuscitation monitoring. In one embodiment, regional saturation of primary organs, such as the brain, may be higher than regional saturation of secondary organs at the onset of shock as blood is diverted away from secondary organs and towards the brain. Accordingly, the present techniques may detect shock early by detecting a change in the regional saturation of secondary organs in the context of normal cerebral oxygenation.

Regional saturation may be used to monitor the oxygen saturation in a patient's brain. Normal or expected values of regional saturation in the brain may indicate that the patient is maintaining appropriate cerebral hemispheric blood oxygen saturation levels. Deviation from normal values may alert a clinician to altered perfusion, particularly when monitoring primary organ perfusion. That is, because shock is characterized by a diversion of blood flow to the brain and away from secondary organs (i.e., gastrointestinal organs), pre shock or early shock may be characterized by relatively normal perfusion of the brain. Further, because shock may involve changes in physiological parameters, the present techniques may also provide additional information to assess shock. In one embodiment, a cerebral saturation measurement above a threshold (indicating flow of blood to the brain) in the context of a drop in blood pressure may be indicative of shock.

Regional saturation may be determined using a cerebral oximeter, which involves using a non-invasive sensor that passes light through a portion of the patient's tissue and photo-electrically senses the absorption and scattering of light in the tissue. The amount of light that is absorbed and/or scattered is used to estimate the amount of blood constituent in the tissue. The pulsatile component of the oximeter signal may be indicative of an arterial oxygen perfusion (i.e., an absolute blood oxygen saturation level of the whole body), and the non-pulsatile component of the signal may be indicative of a regional or local perfusion (i.e., regional saturation of the interrogated region in the body).

With this in mind, FIG. 1 depicts an embodiment of a patient monitoring system 10 that may be used in conjunction with a medical sensor 12. Although the depicted embodiments relate to sensors for use on a patient's forehead and/or temple, it should be understood that, in certain embodiments, the features of the sensor 12 as provided herein may be incorporated into sensors for use on other tissue locations, such as the finger, the toes, the heel, the ear, or any other appropriate measurement site. In addition, although the embodiment of the patient monitoring system 10 illustrated in FIG. 1 relates to photoplethysmography or oximetry, the system 10 may be configured to obtain a variety of medical measurements with a suitable medical sensor. For example, the system 10 may, additionally be configured to determine patient electroencephalography (e.g., a bispectral index), or any other suitable physiological parameter. As noted, the system 10 includes the sensor 12 that is communicatively coupled to a patient monitor 14. The sensor 12 includes one or more emitters 16 and one or more detectors 18. The emitters 16 and detectors 18 of the sensor 12 are coupled to the monitor 14 via a cable 24 through a plug coupled to a sensor port. Additionally, the monitor 14 includes a monitor display 20 configured to display information regarding the physiological parameters, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing the techniques discussed herein.

The monitor 14 may be any suitable monitor, such as an oximetry monitor and/or regional saturation monitor available from Nellcor Puritan Bennett LLC. Furthermore, to upgrade conventional operation provided by the monitor 14 to provide additional functions, the monitor 14 may be coupled to a multi-parameter patient monitor 26 via a cable 32 connected to a sensor input port or via a cable 34 connected to a digital communication port. In addition to the monitor 14, or alternatively, the multi-parameter patient monitor 26 may be configured to calculate physiological parameters and to provide a central display 28 for the visualization of information from the monitor 14 and from other medical monitoring devices or systems. The multi-parameter monitor 26 includes a processor that may be configured to execute code. The multi-parameter monitor 26 may also include various input components 30, such as knobs, switches, keys and keypads, buttons, etc., to provide for operation and configuration of the a multi-parameter monitor 26. In addition, the monitor 14 and/or the multi-parameter monitor 26 may be connected to a network to enable the sharing of information with servers or other workstations. In one embodiment, the sensor 12 may include a sensor body 36 housing the optical components (e.g., an emitter for emitting light at certain wavelengths into a tissue of a patient and a detector for detecting the light after it is reflected and/or absorbed by the blood and/or tissue of the patient) of the sensor. The sensor body 36 may be formed from any suitable material, including rigid or conformable materials, such as fabric, paper, rubber or elastomeric compositions (including acrylic elastomers, polyimide, silicones, silicone rubber, celluloid, PMDS elastomer, polyurethane, polypropylene, acrylics, nitrile, PVC films, acetates, and latex).

In certain embodiments, the sensor 12 may be a wireless sensor 12. Accordingly, the wireless sensor 12 may establish a wireless communication with the patient monitor 14 and/or the multi-parameter patient monitor 26 using any suitable wireless standard. By way of example, the wireless module may be capable of communicating using one or more of the ZigBee standard, WirelessHART standard, Bluetooth standard, IEEE 802.11x standards, or MiWi standard. In embodiments in which the sensor 12 is configured for wireless communication, the strain relief features of the cable 24 may be housed in the sensor body 36.

In the depicted embodiment, the sensor 12 may be a multi-purpose sensor suitable for detection of a plurality of physiological parameters. However, it should be understood that the system 10 may be used in conjunction with separate oximetry and regional saturation sensors 12 (i.e., sensors 12 implemented with separate sensor bodies that may also include respective separate electrical connections to the monitor 14). The sensor 12 may include optical components (e.g., one or more emitters 16 and detectors 18). In one embodiment, the sensor 12 may be configured for photo-electric detection of blood and tissue constituents. For example, the sensor 12 may include pulse oximetry sensing functionality for determining the oxygen saturation of blood as well as other parameters from the plethysmographic waveform detected by the oximetry technique. An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured and other physiological parameters such as the pulse rate and when each individual pulse occurs. Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. At least two, e.g., red and infrared (IR), wavelengths may be used because it has been observed that highly oxygenated blood will absorb relatively less red light and more infrared light than blood with a lower oxygen saturation. However, it should be understood that any appropriate wavelengths, e.g., green, etc., may be used as appropriate. Further, photoplethysmography measurements may be determined based on only one or three or more wavelengths of light.

In addition, the sensor 12 may include regional oximetry functionality. In regional oximetry, by comparing the intensities of at least two wavelengths of light, it is possible to estimate the blood oxygen saturation of hemoglobin in a region of a body. Whereas pulse oximetry measures blood oxygen based on changes in the volume of blood due to pulsing tissue (e.g., arteries), regional oximetry typically examines blood oxygen saturation within the venous, arterial, and capillary systems within a region of a patient. For example, a regional oximeter may include a sensor to be placed on a patient's forehead and may be used to calculate the oxygen saturation of a patient's blood within the venous, arterial and capillary systems of a region underlying the patient's forehead (e.g., in the cerebral cortex). The sensor may include two emitters 44 and 46 (e.g., for emitting two wavelengths of light) and two detectors: one detector that is relatively "close" to the two emitters and another detector that is relatively "far" from the two emitters. Light intensity of multiple wavelengths may be received at both the "close" and the "far" detectors. For example, if two wavelength were used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull is subtracted out, to produce an $rSO_2$ value for deeper tissues. Other methods to calculate regional blood oxygen saturation, such as those provided in U.S. Pat. Nos. 5,139, 025 and 5,217,013 or U.S. Patent Publication No. 20110112387, filed Nov. 12, 2009, the disclosures of which are incorporated by reference in their entirety herein for all purposes, may be employed.

In one embodiment, the regional saturation may be determined in the following manner. Ff $I_A$ represents the intensity of the received/detected light associated with the "close" detector, $$I_A(\lambda,t)/I_o(\lambda)$$

may be derived using Lambert-Beer's law. Similarly, if $I_B$ represents the intensity of the received/detected light associated with the "far" detector, $$I_B(\lambda,t)/I_o(\lambda)$$

may be derived using Lambert-Beer's law. The two or more signals may be derived for a variety of light wavelengths, $\lambda$.

The two derived signals may then be subtracted from each other and processed to arrive at a regional saturation value that pertains to the additional tissue through which the light received at the "far" detector passed (tissue in addition to the tissue through which the light received by the "close" detector passed, e.g., the brain tissue), when it was transmitted through a region of a patient (e.g., a patient's cranium).

In addition to pulse oximetry and regional saturation measurements, the sensors 12 as provided may be configured to monitor other physiological parameters via the optical elements that are configured for pulse oximetry and/or regional saturation monitoring. For example, the sensor 12 may also be configured to detect respiration rate, continuous non-invasive blood pressure (CNIBP), tissue water fraction, water fractions, hematocrit, carboxyhemoglobin, met-hemoglobin, total hemoglobin, fractional hemoglobin, intravascular dyes, and/or water content. For example, in one embodiment, the monitor 10—may be configured to determine a non-invasive blood pressure measurement based on a plethysmographic waveform signal as disclosed in U.S. Patent Application No. 20090326386 to Sethi et al. and assigned to Nellcor Puritan Bennett Ireland and which is incorporated by reference herein in its entirety for all purposes. Accordingly, the monitor 10 may use a plethysmographic waveform signal generated by one or more detectors 18 to determine a blood pressure parameter. In one embodiment, the measurement may be determined by determining a time difference between two characteristic points in the PPG signal that may include, for example, the turning points of 1st, 2nd, 3rd (or any other) derivative of the PPG signal, points of inflection in the PPG signal (or in any suitable derivative thereof), stationary points in the PPG signal (or in any suitable derivative thereof), and any suitable peak or valley in the PPG signal and/or in some derivative of the PPG signal. In some embodiments, adjacent peaks (or adjacent valleys) are used as characteristic points in the PPG signal. In addition, the sensor 12 may include additional functionality, such as temperature or pressure sensing functionality. Further, the system 10 may also be capable of working in conjunction with additional medical monitoring devices, such as non-invasive blood pressure monitoring cuffs, etc.

Figure 2:
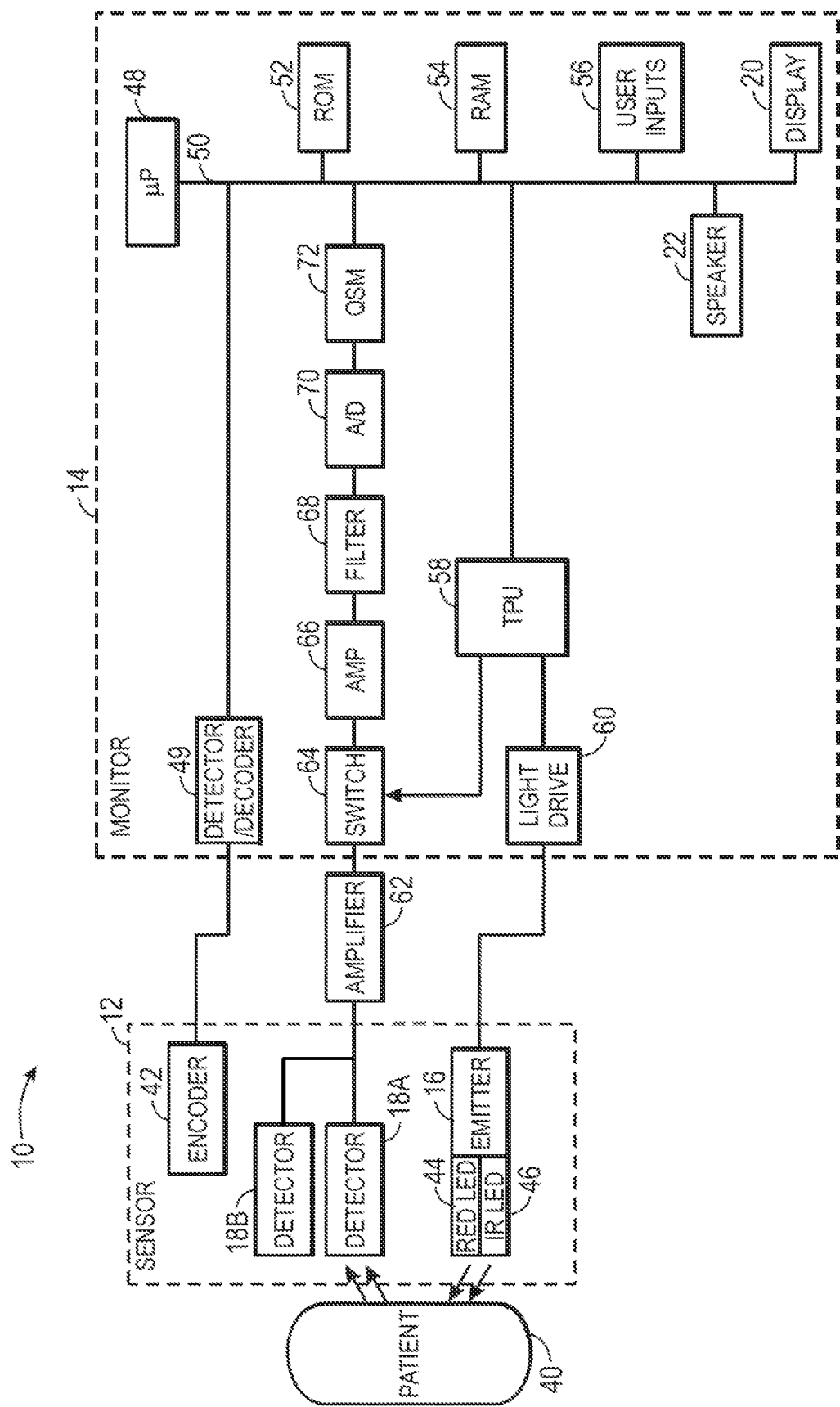
FIG. 2 is a block diagram of the monitoring system of FIG. 1.

Turning to FIG. 2, a simplified block diagram of the medical system 10 is illustrated in accordance with an embodiment. The sensor 12 may include optical components in the forms of emitters 16 and detectors 18 arranged for regional oximetry. The emitter 16 and the detector 18 may be arranged in a reflectance or transmission-type configuration with respect to one another. However, in embodiments in which the sensor 12 is configured for use on a patient's forehead, the emitters 16 and detectors 18 may be in a reflectance configuration. An emitter 16 may also be a light emitting diode, superluminescent light emitting diode, a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the sensor 12 via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. In one embodiment, the emitter 16 may be configured for use in a regional saturation technique. To that end, the emitter 16 may include two light emitting diodes (LEDs) 44 and 46 that are capable of emitting at least two wavelengths of light, e.g., red or near infrared light. In one embodiment, the LEDs emit light in the range of 600 nanometers to about 1000 nm. In a particular embodiment, the LED 44 is capable of emitting light at 730 nm and the other LED 46 is capable of emitting light at 810 nm.

In addition, the sensor 12 may include one or more emitters 16 configured for traditional pulse oximetry. In one embodiment, the emitter 16, including the LEDs 44 and 46, is used for both regional oximetry and pulse oximetry. Further, one or both of the detectors 18a and 18b may also be configured for pulse oximetry. In other embodiments, the pulse oximetry and regional saturation functions are performed by separate optical element sets. It should be noted that the emitter 16 may be capable of emitting at least two wavelengths of light, e.g., red and infrared (IR) light, into the tissue of a patient, where the red wavelength may be between about 600 nanometers (nm) and about 700 nm, and the IR wavelength may be between about 800 nm and about 1000 nm. The emitter 16 may include a single emitting device, for example, with two LEDs 44 and 46, or the emitter 16 may include a plurality of emitting devices with, for example, multiple LED's at various locations. In some embodiments, the LEDs of the emitter 16 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths may include, for example, wavelengths of between approximately 500-600 nm and/or 1000-1100 nm. Regardless of the number of emitting devices, light from the emitter 16 may be used to measure, for example, oxygen saturation, water fractions, hematocrit, or other physiologic parameters of the patient. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In any suitable configuration of the sensor 12, the detectors 18 may be an array of detector elements that may be capable of detecting light at various intensities and wavelengths. In one embodiment, light enters the detector 18 (e.g., detector 18a or 18b) after passing through the tissue of the patient. In another embodiment, light emitted from the emitter 16 may be reflected by elements in the patent's tissue to enter the detector 18. The detector 18 may convert the received light at a given intensity, which may be directly related to the absorbance and/or reflectance of light in the tissue of the patient, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. After converting the received light to an electrical signal, the detector 18 may send the signal to the monitor 14, where physiological characteristics may be calculated based at least in part on the absorption and/or reflection of light by the tissue of the patient.

In certain embodiments, the medical sensor 12 may also include an encoder 42 that may provide signals indicative of the wavelength of one or more light sources of the emitter 16, which may allow for selection of appropriate calibration coefficients for calculating a physical parameter such as blood oxygen saturation. The encoder 42 may, for instance, be a coded resistor, EEPROM or other coding devices (such as a capacitor, inductor, PROM, RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 42 may include encryption coding that prevents a disposable part of the medical sensor 12 from being recognized by a microprocessor 48 unable to decode the encryption. For example, a detector/decoder 49 may translate information from the encoder 50 before it can be properly handled by the processor 48. In some embodiments, the encoder 42 and/or the detector/decoder 48 may not be present. In embodiments in which the oximetry and regional saturation functionality are present in separate sensors, each sensor 12 may include its own encoder 42.

Signals from the detector 18 and/or the encoder 47 may be transmitted to the monitor 14 via input circuitry configured to receive the sensor signals and provide the received signals to one or more processors 48 coupled to an internal bus 50. Also connected to the bus may be a ROM memory 50, a RAM memory 54 and a display 20. A time processing unit (TPU) 58 may provide timing control signals to light drive circuitry 60, which controls when the emitter 16 is activated, and if multiple light sources are used, the multiplexed timing for the different light sources. It is envisioned that the emitters 16a and 16b may be controlled via time division multiplexing of the light sources. TPU 58 may also control the gating-in of signals from detector 18 through a switching circuit 64. These signals are sampled at the proper time, depending at least in part upon which of multiple light sources is activated, if multiple light sources are used. The received signal from the detector 18 may be passed through an amplifier 66, a low pass filter 68, and an analog-to-digital converter 70 for amplifying, filtering, and digitizing the electrical signals the from the ear sensor 12. The digital data may then be stored in a queued serial module (QSM) 72, for later downloading to RAM 52 as QSM 72 fills up. In an embodiment, there may be multiple parallel paths for separate amplifiers, filters, and A/D converters for multiple light wavelengths or spectra received.

In an embodiment, based at least in part upon the received signals corresponding to the light received by detector 18, processor 48 may be programmed to calculate one or more of the regional saturation, oxygen saturation, and blood pressure using various algorithms. These algorithms may use coefficients, which may be empirically determined. For example, algorithms relating to the distance between an emitter 16 and various detector elements in a detector 18 may be stored in a ROM 52 and accessed and operated according to processor 48 instructions.

Furthermore, one or more functions of the monitor 14 may also be implemented directly in the sensor 12. For example, in some embodiments, the sensor 12 may include one or more processing components capable of calculating the physiological characteristics from the signals obtained from the patient. In accordance with the present techniques, the sensor 12 may be configured to provide optimal contact between a patient and the detector 18, and/or the emitter 16. The sensor 12 may have varying levels of processing power, and may output data in various stages to the monitor 14, either wirelessly or via the cable 24. For example, in some embodiments, the data output to the monitor 14 may be analog signals, such as detected light signals (e.g., pulse oximetry signals or regional saturation signals), or processed data.

The system 10 may be used for detecting and managing patients with shock. Accordingly, the disclosed embodiments may include patient monitoring as well as techniques for providing instructions or alerts to caregivers related to whether a patient is likely to be in shock. Further, the techniques may include assessments of the success of intervention or treatment for patients who are suspected to be in shock. Such assessments may include monitoring regional saturation, either alone or in combination with other physiological parameters, to determine if a treatment for shock, such as fluid therapy, has been effective.

Figure 3:
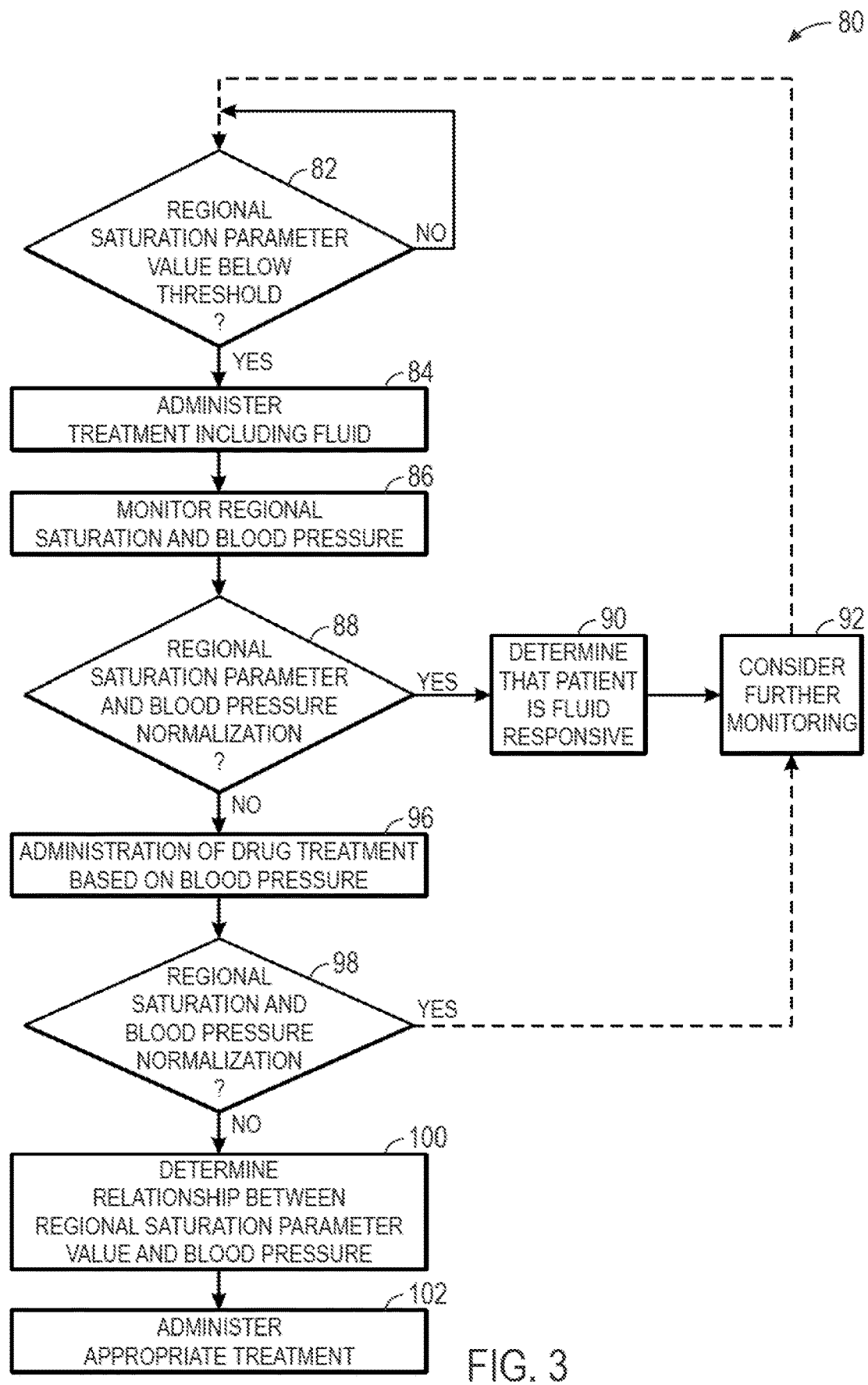
FIG. 3 is a flow diagram of a method illustrating an embodiment.

FIG. 3 is an exemplary process flow diagram illustrating a method for detection of shock. The method is generally indicated by reference number 80 and includes various steps or actions represented by blocks. It should be noted that the method 80 may be performed as an automated or semiautomated procedure by a system, such as system 10. Further, certain steps or portions of the method may be performed by separate devices. For example, a portion of the method 80 may be performed by a clinician, while a second portion of the method 80 may be performed by a monitor 14. In embodiments, the method 80 may be performed continuously or intermittently for long-term patient monitoring or at any appropriate interval depending on the particular situation of the monitored patient.

According to a presently contemplated embodiment, the method 80 receives regional saturation parameter information from a sensor on the patient and determines if the parameter value is below a predetermined threshold at step 82. If the value is above the threshold or goal, the method 80 continues with monitoring and returns to step 82. However, values below the threshold may indicate early onset shock. In such cases, the system 10 may provide a warning or alarm to prompt a caregiver to administer a treatment for shock, which includes administering a fluid bolus at step 82. Other shock treatments may include treatment according to adult or pediatric advanced life support guidelines (PALS), oxygen, support ventilation, and vascular access. In one embodiment, the PALS guidelines may include administration of 20 ml/kg/boluses of isotonic fluid within the first hour of detection. Accordingly, early detection of shock may facilitate earlier intervention. Additional guidelines under PALS include correcting hypoglycemia and hypocalcemia, administration of antibiotics, vasopressor drip, and stress dose of hydrocortisone before determining if the patient is fluid-responsive.

During the intervention and after the treatment, the patient's regional saturation and blood pressure are monitored at step 86. If at least the regional saturation returns to normal levels (e.g., at or above threshold) at step 88, the patient may be considered to be fluid-responsive at step 90, and the patient may be monitored further to assess continued stabilization at step 92. For example, the method 80 may return to step 82 for continued regional saturation monitoring at step 82. In one embodiment, the assessment at step 88 may occur within an hour of starting the administration of fluid therapy.

It should be understood that the method 80 may consider only a drop in regional saturation in the context of normal blood pressure as a sign of shock. In other embodiments, the drop in regional saturation may be accompanied by a concurrent drop in blood pressure. Normalization may involve return of regional saturation, blood pressure, or both to normal levels. If the regional saturation parameter value is determined to not normalize at step 88, additional treatment may be administered at step 96. Such treatment may include vasoactive drug therapy and titration to correct hypotension and poor perfusion. Here, the blood pressure information may be used to determine the appropriate treatment. For example, if the regional saturation parameter value is low in the context of normal blood pressure, appropriate treatment may include dopamine. For low blood pressure and suspected warm shock (e.g., high cardiac output and vasodilation), which may be anaphylactic shock, norepinephrine may be administered while for patients with suspected cold shock (e.g., later stage shock, decreased cardiac output, selective vasoconstriction), epinephrine may be administered.

If, after administration of therapy at step 96, the regional saturation parameter, and, in certain embodiments, the blood pressure normalizes at step 98, the method 80 may return to step 92 for further patient monitoring. Otherwise, for low regional saturation, with or without concurrent low blood pressure, the method 80 may determine appropriate treatment based on a relationship between the regional saturation and the blood pressure at step 100 and administer the appropriate treatment at step 102 accordingly.

Figure 4:
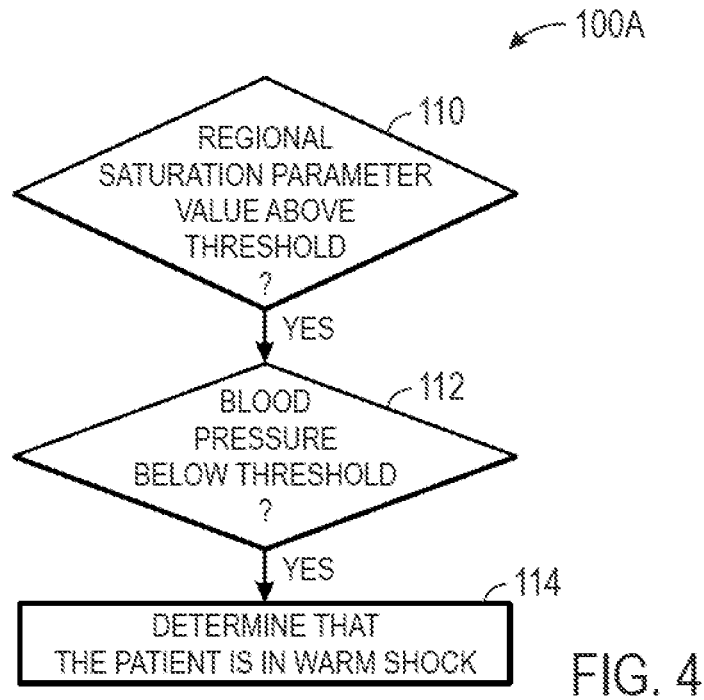
FIG. 4 is a flow diagram of a method illustrating an embodiment.
Figure 5:
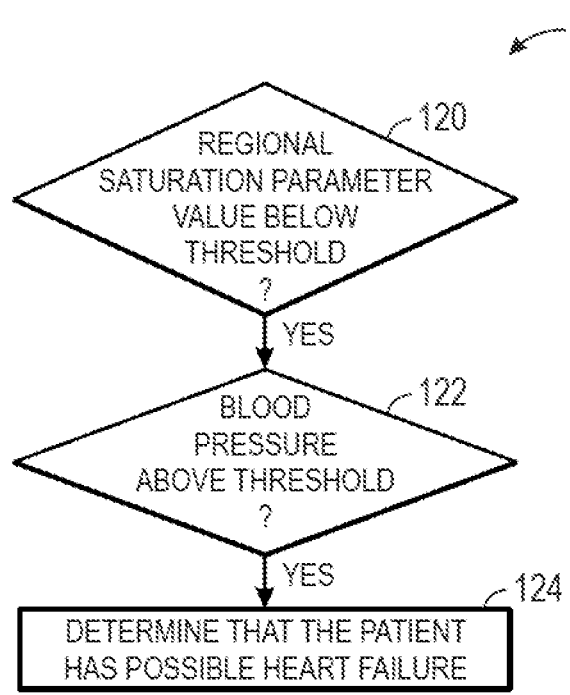
FIG. 5 is a flow diagram of a method illustrating an embodiment.
Figure 6:
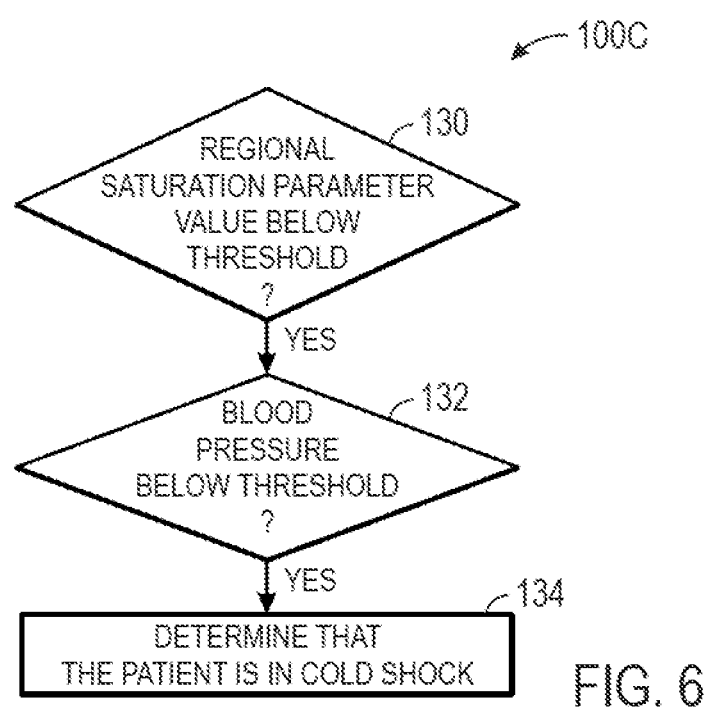
FIG. 6 is a flow diagram of a method illustrating an embodiment.

For example, as shown in FIG. 4, step 100 may include the steps of 100*a* if the regional saturation parameter value is determined to be above the threshold at step 110 and the blood pressure is determined to be below the threshold at step 112. In such a case, the patient is determined to be in warm shock. For a patient in warm shock, appropriate treatment at step 102 may include vasoconstrictive drugs, such as norepinephrine and vasopressin. Fluid boluses may also be given. In another embodiment, as shown in FIG. 5, step 100 may include the steps of 100*b* if the regional saturation parameter value is determined to be below the threshold at step 120 and the blood pressure is determined to be above the threshold at step 122. In such a case, the patient may be in heart failure. The appropriate treatment at step 102 may include transfusions to Hgb of greater than 10 g/dL, optimizing $SpO_2$, additional fluid, and drugs such as milrinone, nitroprusside, or dobutamine. As shown in FIG. 6, step 100 may include the steps of 100*c* if the regional saturation parameter value is determined to be below the threshold at step 130 and the blood pressure is determined to be below the threshold at step 132. In such a case, the patient may be in cold shock. The appropriate treatment at step 102 may include transfusions to Hgb of greater than 7 g/dL, optimizing $SpO_2$, additional fluid, and drugs such as epinephrine or dobutamine and norepinephrine.

Figure 7:
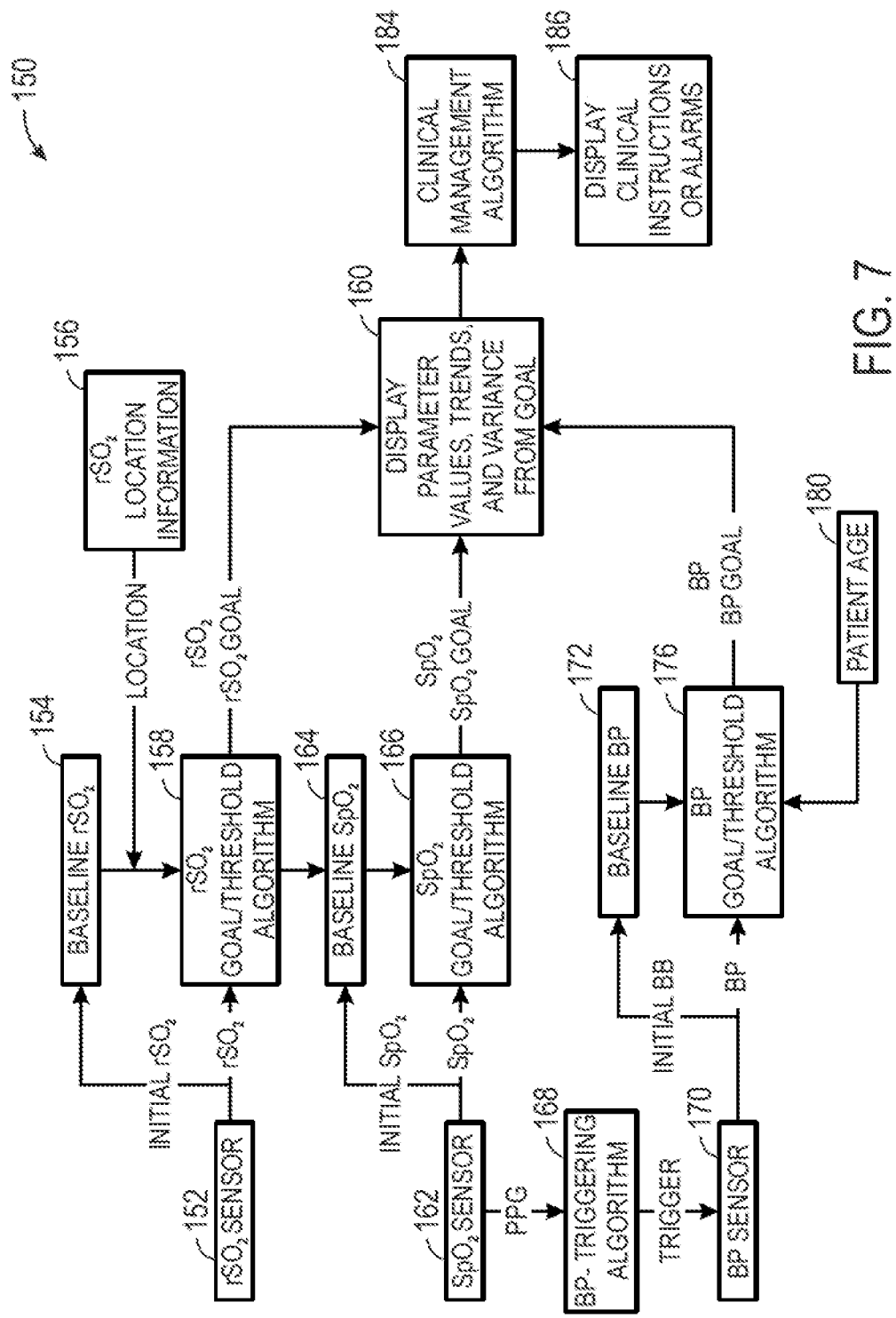
FIG. 7 is a block diagram of a system for monitoring multiple parameters to detect shock according to an embodiment of the present disclosure.

While the determination of whether a patient is fluid-responsive or whether that patient may have shock may be made with the information from regional saturation monitoring, the use of multiple parameters (e.g., blood pressure) may provide additional information that may determine which type of shock may be present or what therapies may be most appropriate. To that end, FIG. 7 shows a system 150 for facilitating clinical management that may be used in conjunction with or part of the system 10 (see FIG. 1). In certain embodiments, the system 150 may include one or more sensors 12, such as a regional saturation sensor, that provides input to a clinical management algorithm for providing instructions or care suggestions for patient with shock.

For example, the system 150 may include one or more $rSO_2$ sensors 152 that are controlled by the system 150 and that generate a signal from which a regional saturation parameter value can be determined. The $rSO_2$ sensor 152 may provide calibration or baseline regional saturation at block 154. In addition, the system 152 may consider sensor location information 156. Such information may be manually input by a caregiver or may be accessed from an encoder (e.g., encoder 42) associated with the sensor 152. That is, the encoder may store information about the appropriate sensor location for a particular sensor model or type. Both the baseline regional saturation 154 and the location information 156 may be considered in the regional saturation goal or threshold algorithm 158. For example, in certain embodiments, the regional saturation may be associated with different goals depending on the location of the sensor. Such goals for regional saturation or other parameters may be displayed, along with the measured parameter value, via a display at block 160.

Present embodiments may include a non-invasive regional saturation threshold of 60% or 50-60% for detecting shock. That is, regional saturation below a threshold of 60% or 50-60% may be considered a risk factor for shock or developing shock and, for patients below the threshold, a goal of therapy may be normalizing regional saturation to levels at or above the preset threshold. Alternatively, the threshold may be set to the baseline regional saturation 154 if the patient is considered to relatively stable at the time the baseline was taken. Further, a patient below threshold and at risk for shock or in shock may be a patient with a measured regional saturation below the baseline or a regional saturation that is trending away from baseline at a predetermined rate. For example, a patient may be at risk for shock if the regional saturation trend over a period of time is generally downward, even at measured values at or above the threshold. In one embodiment, the regional saturation measurement threshold may be used to determine if corroborating measurements via central or mixed venous catheterization are warranted. For example, if the patient is normotensive (i.e., normal blood pressure) and has adequate end-organ perfusion as shown by a measured $rSO_2$ of greater than 60%-70%, a central or mixed venous catheter may be delayed until the clinical condition indicates the need for vasopressors.

The thresholds and goals may be different depending on the location information 156 associated with the sensor 152. For example, an individual patient may tend to have generally higher renal and abdominal regional saturation values relative to cerebral values. Accordingly, the cerebral regional saturation goal may be established as a higher threshold relative to goals for renal or abdominal regional saturation. However, measured values for each sensor location may also experience different degrees of variability. Further, at block 158, the system 150 may take sensor location information into account when assessing changes in $rSO_2$ that are associated shock. In embodiments in which multiple regional saturation sensors 152 are applied to a patient at different locations (e.g., for cerebral, renal, and abdominal $rSO_2$ monitoring), a decline in secondary organ regional saturation may precede changes in cerebral regional saturation. In one embodiment, a patient in pre-shock may be characterized by a relatively stable cerebral $rSO_2$ in the context of decreasing abdominal and/or renal $rSO_2$. As shock progresses, the cerebral regional saturation may also decrease. Accordingly, declining cerebral regional saturation parameter values lagging similar declines in the regional saturation values at other locations may be used to assess the progression of shock. Alternatively, normalization of abdominal or renal regional saturation before a decline in cerebral regional saturation may be indicative of the success of shock intervention. The system 150 may be configured to provide assessments of shock based on comparing measurements and trends at different sensor locations.

In one embodiment, the system 152 also includes a pulse oximetry or $SpO_2$ sensor 162. As discussed herein, the pulse oximetry sensor 162 may be part of a unitary sensor body that also performs regional saturation measurements, either with or without shared optical components for both functions, or may be a separate sensor structure. The pulse oximetry sensor 162 may provide baseline measurements 164 and ongoing monitored measurements as an input to an $SpO_2$ goal or threshold algorithm, which in turn are provided to addition processing blocks for display (block 160) and/or consideration in clinical management for patient care. The oxygen saturation values may reflect the general availability of oxygen, which may provide information about the success of breathing interventions. In embodiments in which the system 150 includes a blood pressure sensor 170 coupled to a cuff, the PPG generated by the $SpO_2$ sensor 162 may be used to trigger the cuff measurements via the blood pressure sensor 170 through a blood pressure triggering algorithm 168. In such an embodiment, inflation of the cuff to oversystolic pressure results in cessation of a detected pulse waveform at the photoplethysmography sensor, because blood flow to the tissue under the cuff is restricted. As the cuff is deflated and the blood begins to flow into the tissue, the pulse waveform resumes and is able to be detected by the photoplethysmography sensor. The cuff pressure at which the pulse waveform reemerges via sensor measurements correlates to the systolic pressure. In this manner, photoplethysmography signals may be used to determine the systolic pressure. From the systolic pressure as well as the mean arterial pressure, a patient's systolic and diastolic blood pressure may be determined. The blood pressure triggering algorithm 168 may be configured to inflate the cuff to oversystolic by detecting the pressure at which the PPG cannot be detected and may be configured to subsequently deflate the cuff to the pressure at which the PPG reappears. The baseline blood pressure and measured blood pressure is provided to a blood pressure goal/threshold algorithm, which may also take into account the patient's age 180.

As depicted, the measured parameters as well as the goal/threshold information for the measured parameter/s in the system 150 may displayed at block 160 along with appropriate numerical indicators, values etc. In one embodiment, the parameter values (e.g., regional saturation, oxygen saturation, blood pressure) as disclosed herein may include single values representative of one time point or values collected over a predetermined time window to assess changes that are averaged or combined. For example, the parameter values may be assessed as a rolling average during a time window. Further, it is contemplated that a display 20 of the monitor 14 may provide a visual representation of parameter values and may provide visual information to clinicians regarding a change in a patient's clinical condition. Other indications, such as graphical or audio indications, are also contemplated. Further, the system 10 may provide a numeric value or a green light indicated on a display or a short tone generated by a speaker associated with monitor 14 if the regional saturation value is at or above the threshold. Similarly, a regional saturation value associated with shock (i.e., below the threshold) may trigger an alarm, which may include one or more of an audio or visual alarm indication. In one embodiment, the alarm may be triggered if the regional saturation value is substantially greater than a predetermined value or outside of a predetermined range. In addition, the system 150 may determine trend values for increasing or decreasing parameter values as well as variability indices.

The system 150 may also provide the parameter values, baseline information, and/or any predetermined goals/thresholds as inputs to a clinical management algorithm 184. The clinical management algorithm 184 may assess the regional saturation values, with or without additional parameter information, to determine whether the patient is in shock or has responded to shock therapy. For example, the clinical management algorithm may assess a relationship between the regional saturation and the blood pressure as provided herein. Based on the information, the system 150 may provide additional indications, alarms, or instruction at block 186.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A system comprising:
   input circuitry configured to receive a regional saturation signal from a regional saturation sensor and a blood pressure signal from blood pressure sensor; and
   a processor configured to:
      determine a regional saturation parameter of a patient based on the regional saturation signal;
      determine a blood pressure parameter of the patient based on the blood pressure signal;
      determine the patient is in shock;
      determine a treatment for the shock by at least comparing the regional saturation parameter to a first threshold and comparing the blood pressure parameter to a second threshold; and
      provide an output based on the determined treatment.

2. The system of claim 1, further comprising a medical device configured to deliver the treatment to the patient, wherein the processor is configured provide the output by at least controlling the medical device to administer the treatment to the patient.

3. The system of claim 2, wherein the processor is configured to control the medical device to administer the treatment to the patient by at least controlling the medical device to deliver a drug to the patient.

4. The system of claim 1, wherein the processor is configured to determine the treatment by at least:
   determining the regional saturation parameter is above the first threshold;
   determining the blood pressure parameter is below the second threshold; and
   selecting a warm shock treatment for the patient in response to determining the regional saturation parameter is above the first threshold and determining the blood pressure parameter is below the second threshold.

5. The system of claim 4, further comprising a medical device, wherein the processor is configured provide the output by at least controlling the medical device to administer the warm shock treatment by at least controlling the medical device to deliver at least one of a vasoconstrictive drug or a fluid bolus to the patient.

6. The system of claim 1, wherein the processor is configured to determine the treatment by at least:
   determining the regional saturation parameter is below the first threshold;
   determining the blood pressure parameter is below the second threshold; and
   selecting a cold shock treatment for the patient in response to determining the regional saturation parameter is below the first threshold and determining the blood pressure parameter is below the second threshold.

7. The system of claim 6, further comprising a medical device, wherein the processor is configured provide the output by at least controlling the medical device to administer the cold shock treatment by at least controlling the medical device to deliver at least one of:
   hemoglobin of greater than 7 grams per deciliter (g/dL) to the patient;
   fluid to the patient to the patient;
   epinephrine to the patient; or
   dobutamine and norepinephrine to the patient.

8. The system of claim 1, wherein the processor is configured to determine the patient is shock by at least:
   comparing the regional saturation parameter to the first threshold;
   comparing the blood pressure parameter to the second threshold; and
   determining that the patient is in shock based on the comparison of the regional saturation parameter to the first threshold and the comparison of the blood pressure parameter to the second threshold.

9. The system of claim 1, wherein the processor is configured to determine the first threshold value based on a location of the regional saturation sensor on the patient.

10. The system of claim 9, wherein the processor is configured to determine the first threshold value based on the location of the regional saturation sensor on the patient by at least:
    determining the regional saturation sensor is at a cerebral location and selecting a first regional saturation threshold value in response to determining the regional saturation sensor is at the cerebral location; or
    determining the regional saturation sensor is at a renal location or an abdominal location on the patient and selecting a second regional saturation threshold value in response to determining the regional saturation sensor is at the renal location or the abdominal location, wherein the first regional saturation threshold value is higher than the second regional saturation threshold.

11. The system of claim 1, wherein the regional saturation parameter or the blood pressure parameter is a single value representative of one time point or a plurality of values collected over a predetermined time window.

12. The system of claim 1, wherein the regional saturation sensor comprises a first regional saturation sensor and the regional saturation signal comprises a first regional saturation signal, the input circuitry being configured to receive a second regional saturation signal from a second regional saturation sensor, wherein the processor is configured to:
    determine the first regional saturation signal indicates a stable cerebral regional oxygen saturation;
    determine the second regional saturation signal indicates a decreasing abdominal or renal regional oxygen saturation; and
    determine the patient is in pre-shock in response to determining the first regional saturation signal indicates a stable cerebral regional oxygen saturation and the second regional saturation signal indicates a decreasing abdominal or renal regional oxygen saturation.

13. The system of claim 1, wherein the regional saturation sensor comprises a first regional saturation sensor and the regional saturation signal comprises a first regional saturation signal, the input circuitry being configured to receive a second regional saturation signal from a second regional saturation sensor, wherein the processor is configured to:
    determine that the first regional saturation signal indicates declining cerebral regional oxygen saturation;
    determine that the second regional saturation signal indicates a normalizing abdominal or renal regional oxygen saturation; and
    determine a shock intervention provided to the patient was successful in response to determining the first regional saturation signal indicates declining cerebral regional oxygen saturation and the second regional saturation signal indicates a normalizing abdominal or renal regional oxygen saturation.

14. The system of claim 1, further comprising a display, wherein the processor is configured to provide the output by at least presenting information indicative of the determined treatment via the display.

15. The system of claim 1, further comprising an audio device, wherein the processor is configured to provide the output by at least outputting information indicative of the determined treatment via the audio device.

16. The system of claim 1, wherein the processor is configured to determine the treatment by at least:
    determining the regional saturation parameter is below the first treatment threshold;
    determining the blood pressure parameter is above the second treatment threshold; and
    selecting a heart failure treatment for the patient in response to determining the regional saturation parameter is below the first threshold and determining the blood pressure parameter is above the second threshold.

17. A method comprising:
    determining, by a processor, a regional saturation parameter of a patient based on a regional saturation signal from a regional saturation sensor;
    determining, by the processor, a blood pressure parameter of the patient based on a blood pressure signal from blood pressure sensor;
    determining, by the processor, the patient is in shock;
    determining, by the processor, a treatment for the shock, wherein determining the treatment comprises comparing the regional saturation parameter to a first threshold and comparing the blood pressure parameter to a second threshold; and
    providing, by the processor, an output based on the determined treatment.

18. The method of claim 17, wherein providing the output comprises controlling a medical device to administer the treatment to the patient.

19. The method of claim 17, wherein determining the treatment comprises:
    determining the regional saturation parameter is above the first threshold;
    determining the blood pressure parameter is below the second threshold; and
    selecting a warm shock treatment for the patient in response to determining the regional saturation parameter is above the first threshold and determining the blood pressure parameter is below the second threshold.

20. The method of claim 17, wherein determining the treatment comprises:
  determining the regional saturation parameter is below the first threshold;
  determining the blood pressure parameter is below the second threshold; and
  selecting a cold shock treatment for the patient in response to determining the regional saturation parameter is below the first threshold and determining the blood pressure parameter is below the second threshold.

21. The method of claim 17, wherein determining the patient is shock comprises:
  comparing the regional saturation parameter to the first threshold;
  comparing the blood pressure parameter to the second threshold; and
  determining that the patient is in shock based on the comparison of the regional saturation parameter to the first threshold and the comparison of the blood pressure parameter to the second threshold.

22. The method of claim 17, further comprising determining, by the processor, the first threshold value based on a location of the regional saturation sensor on the patient.

23. The method of claim 22, wherein determining the first threshold value based on the location of the regional saturation sensor on the patient comprises:
  determining the regional saturation sensor is at a cerebral location and selecting a first regional saturation threshold value in response to determining the regional saturation sensor is at the cerebral location; or
  determining the regional saturation sensor is at a renal location or an abdominal location on the patient and selecting a second regional saturation threshold value in response to determining the regional saturation sensor is at the renal location or the abdominal location, wherein the first regional saturation threshold value is higher than the second regional saturation threshold.

24. The method of claim 17, wherein providing the output comprises presenting information indicative of the determined treatment via a display.

25. The method of claim 17, wherein providing the output comprises outputting information indicative of the determined treatment via an audio device.

26. A system comprising:
  means for determining a regional saturation parameter of a patient based on a regional saturation signal from a regional saturation sensor;
  means for determining a blood pressure parameter of the patient based on a blood pressure signal from blood pressure sensor;
  means for determining the patient is in shock based on the regional saturation parameter and the blood pressure parameter;
  means for determining a treatment for the shock based on a comparison of the regional saturation parameter to a first threshold and a comparison of the blood pressure parameter to a second threshold; and
  means for providing an output based on the determined treatment.

27. The system of claim 26, wherein the means for determining comprises:
  means for determining the first threshold value based on a location of the regional saturation sensor on the patient;
  means for comparing the regional saturation parameter to the first threshold;
  means for comparing the blood pressure parameter to the second threshold; and
  means for determining that the patient is in shock based on the comparison of the regional saturation parameter to the first threshold and the comparison of the blood pressure parameter to the second threshold.

* * * * *